United States Patent [19]
Woodward

[11] Patent Number: 4,696,067
[45] Date of Patent: Sep. 29, 1987

[54] WOMEN'S URINAL FOR USE IN ERECT POSITION

[76] Inventor: Marylou Woodward, 3255 Randall Ave. (Apt. 2H), Bronx, N.Y. 10465

[21] Appl. No.: 912,668

[22] Filed: Sep. 29, 1986

Related U.S. Application Data

[63] Continuation-in-part of Ser. No. 646,472, Aug. 30, 1984, abandoned, which is a continuation-in-part of Ser. No. 614,877, May 29, 1984, abandoned.

[51] Int. Cl.$^4$ .......................... A47K 11/00; A61B 5/00
[52] U.S. Cl. ...................................... 4/144.1; 4/144.3; 4/144.4; 128/761
[58] Field of Search .................. 4/144.1, 144.3, 144.2, 4/144.4, 301, 114.1; 128/761; 604/327

[56] References Cited

U.S. PATENT DOCUMENTS

| | | | |
|---|---|---|---|
| 1,407,872 | 2/1922 | Lacy | 4/144.4 |
| 1,928,170 | 9/1933 | Dwork | 4/144.4 |
| 2,734,198 | 2/1956 | Kutsche | 4/144.2 |
| 3,329,973 | 7/1967 | Bobbe | 4/144.4 |
| 3,485,233 | 12/1969 | Cord | 128/761 |
| 3,575,225 | 4/1971 | Muheim | 4/144.3 X |
| 3,629,873 | 12/1971 | Long | 4/144.2 X |
| 3,727,244 | 4/1973 | Collins | 4/144.3 |
| 3,742,523 | 7/1973 | Atkins | 4/144.2 |
| 3,822,419 | 7/1974 | Wilson, Sr. | 4/144.4 X |
| 3,864,759 | 2/1975 | Horiuchi | 4/144.3 |
| 3,900,019 | 8/1975 | Logiadis | 4/144.3 X |
| 3,923,040 | 12/1975 | Beach | 4/144.4 X |
| 3,927,426 | 12/1975 | Geddes | 4/144.3 |
| 3,964,111 | 6/1976 | Packer | 4/144.4 |
| 4,305,161 | 12/1981 | Diaz | 4/144.2 |

Primary Examiner—Henry K. Artis
Attorney, Agent, or Firm—Frishauf, Holtz, Goodman & Woodward

[57] ABSTRACT

When the flexible walls of an open box urinal are pressed together by the thighs of the user, the relatively stiff bottom and the deformed walls hold the container in place without other support during use. The box is sufficiently wide and the walls sufficiently resistant to deformation to deform the user's thighs enough to spread apart her labia that would otherwise be touched by the stream of urine discharged by the urethra and cause post-urination trickle. A handle or lip attached at the wall of the urinal towards the front of the user facilitates placement and removal with one hand.

11 Claims, 5 Drawing Figures

WOMEN'S URINAL FOR USE IN ERECT POSITION

This application is a continuation-in-part of application Ser. No. 646,472, filed Aug. 30, 1984, which was a continuation-in-part of application Ser. No. 614,877, filed May 29, 1984, both now abandoned.

This invention is a urinal for women to make it unnecessary for a woman to sit or squat in order to urinate, as may be advantageous for women suffering from arthritis or varicose veins or convenient for women active in narrow quarters or where sanitary facilities, if any, are minimal, as in the case of camping or sailing and generally in wilderness and undeveloped regions, or when it is desired to avoid contact with urban sanitary facilities that are neglected or poorly maintained.

A variety of urinals have been designed for use in hospitals, mostly for use by sitting or reclining patients. Some urinals are designed to be worn by patients whose infirmities make them incontinent. Those for standing use are either in the nature of a container that can be capped to hold a sample for analysis or are in the nature of funnels to aid collection in such a container.

U.S. Pat. No. 3,485,233 shows a funnel shaped to conform with anatomy, and equipped with a stopper, which can be used to collect a small amount of urine for a medical test.

SUMMARY OF THE INVENTION

It is an object of this invention to provide a women's urinal with a capacity sufficient for normal full relief, of a shape suitable for holding between the legs without manual help even when full, easy both to use and to empty and of a kind which when used will deform a female user's thighs enough to spread her labia apart and out of the way of a stream of urine discharged by her urethra.

It has been found that it is not necessary to fit the top of the urinal closely to the crotch and that attempts to do so often result in devices that are so narrow that they let urine escape even when the capacity of the urinal is not so small that overflow is a problem. More significantly, the present invention makes clear that what is needed is not to fit the crotch, but rather to provide a urinal that will spread the thighs near the crotch in resistance to a normal erect stance of the thighs and thereby spread the labia apart, exposing the orifice of a female's urethra so that the urethra can project a direct stream of urine into the urinal receptacle without dribble or trickle into any other area. This contrasts with seated urination, during which the urethra may be deflected or enfolded by the labia, causing urine to trickle over the entire vulva. The medical advantages of erect urination into a urinal according to the invention are important in cases where a clean vulva is essential, as in post-partum care.

According to the invention, the urinal is preferably made of plastic such as polyethylene, polystyrene, or the like, which is tough and flexible enough and stiff enough at the rim so that the upper part can be pressed together by the user's thighs against sufficient resistance to deformation to spread the labia apart as above mentioned while the lower portion of the container, stiffened by the bottom, presses locally into the flesh of the user's thighs to hold the urinal in place and thereby can support the filled receptacle against falling. A cheaper version, designed to be disposable, is made of stiffer material.

In the preferred embodiments of the invention, the urinal is made of a resiliently flexible material and has the shape of an open-top box. The bottom stiffens the box against deformation and deforms the flesh surface of the thighs to keep the urinal from dropping while the upper part yields and is deformed to keep the urinal from tipping while exerting enough spreading force on the thighs to cause the labia to spread apart. The rim is reinforced, as by a molded bead, to help exert the spreading force. The side of the box towards the front of the user joins the lateral walls at a place of full or maximum width and it is at this side that manual folding means may usefully be provided, which, if desired, be a detachable handle. The container cross-section may be square or rectangular and also somewhat tapered to facilitate manufacture and/or storage. In one embodiment, the lateral walls are concave, at least at the bottom, in the unstressed state, and in this case the bottom part can be more easily grasped from the front and a handle would be a redundant feature.

The capacity of the urinal should be at least ¾ liter and preferably about 1 liter for use by an adult. It may be about ½ liter for small children.

BRIEF DESCRIPTION OF THE DRAWINGS

The invention is further described by way of illustrative examples with reference to the annexed drawings, in which:

FIG. 4 is a perspective view and FIG. 5 is a side view, on a smaller of a third embodiment of a urinal according to the invention, in this case made of relatively stiff material.

DESCRIPTION OF THE ILLUSTRATED EMBODIMENTS

Figure 1:
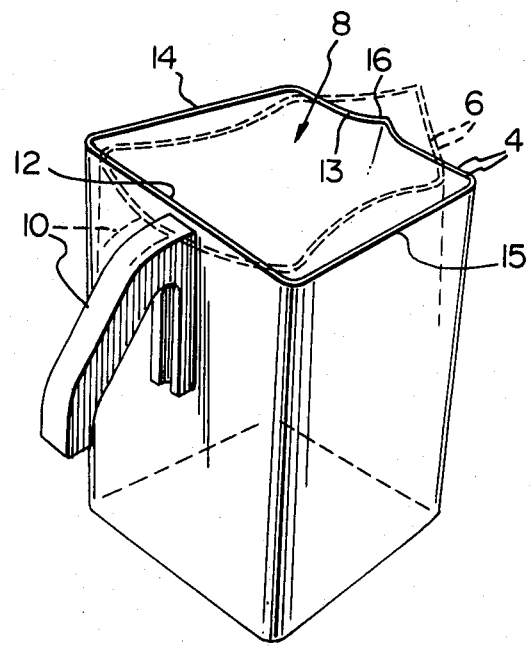
FIG. 1 is a perspective view of a first embodiment of a urinal according to the invention, showing it in the unstressed state in solid lines and as deformed by the user's thighs in broken lines.

FIG. 1 shows a first embodiment of the urinal, the solid lines showing the urinal in its unstressed state and the broken lines 6 in the top part of the drawing indicating the manner in which it is deformed by lateral pressure from the thighs of the user when the device is in use. The deformation when the urinal is inserted between the thighs of the user who is standing in an erect position, is generally somewhat greater than shown in the broken lines at the top of FIG. 1, but the nature of the deformation is more easily understood by reference to the first stage of deformation shown in FIG. 1 and a final stage of deformation, more particularly shown in connection with another embodiment in FIG. 2.

The urinal of FIG. 1 is composed of an open-topped box 8 of resiliently flexible plastic equipped with a handle 10 attached to, and preferably made integral with, the box 8. The box of FIG. 1 has a four-cornered flat base from which four walls arise, the walls including a front wall 12, a rear wall 13 and lateral walls 14 and 15. The terms "front" and "rear" refer respectively to the sides that are towards the front of the person using the device and towards the rear of that person when the device is in use, rather than what would be the front or back when a person is carrying the device around on the way to emptying it. The urinal shown in FIG. 1 is shaped in the middle of the rear wall 13, at the top to provide a pouring lip or spout 16, but this detail is quite unnecessary, since the container can easily be emptied, using one corner to guide the pouring. The opening at the top of the box 8 is, except for the spout 16, of the same shape as the flat base at the bottom, but of slightly larger size so as to provide a small taper to the walls which can facilitate removal of the device from a mold, as well as permit partial nesting of two or more of the device for storage. The shape can be square or rectangular, with the dimension from front to rear being made the larger in the latter case, but since in use of the device it is carried somewhat forward of the middle of the gap between the user's thighs, if the front and rear walls are to be of different width, the greater width should be at the front. In the embodiment shown in FIG. 1, the rear side of the bottom and the rear wall are slightly less wide than the front side of the bottom and the front wall, which is to say that the shape of the bottom and that of the top opening are slightly trapezoidal. The difference in width should not be great, however, because the deformation at the rear wall is much greater when the device is used than the deformation at the front wall, as shown in FIGS. 1 and 2.

Figure 2:
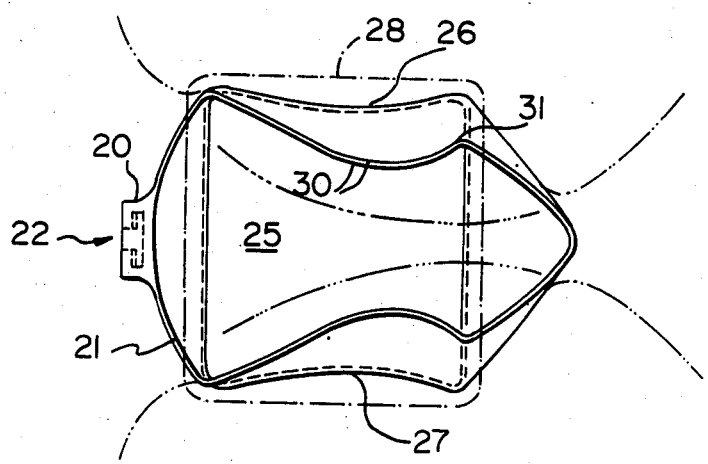
FIG. 2 is a top view and FIG. 3 is a side view of a second embodiment of the urinal according to the invention, showing in solid lines the urinal as deformed by the user's thighs and in broken lines the urinal in its unstressed state.
Figure 3:
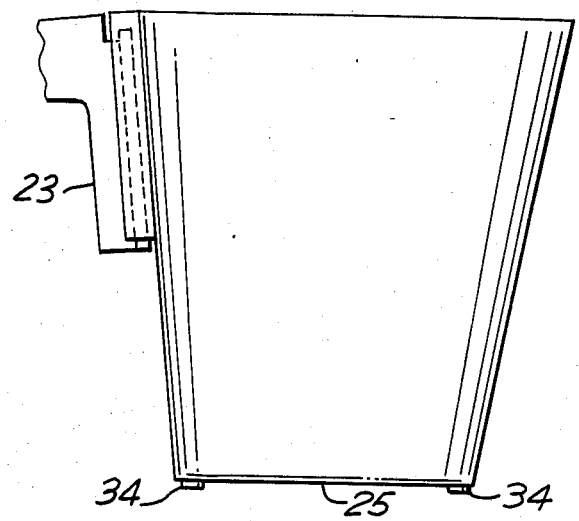

FIG. 2 shows a second embodiment of urinal according to the invention, in a top view, and FIG. 3 shows the same embodiment in a side view. FIGS. 2 and 3 show the shape, in solid lines, which the urinal takes on under pressure of the user's thighs, when it is in place for use. No attempt is made to show any part of the user in FIG. 3, but in FIG. 2 double dotted broken lines show the outline of a cross-section, at the level of the top of the urinal, of the user's thighs where they depart from contact with the top of the urinal and the triple dotted lines show approximately where the contour of the user's thighs would be except for the interposition of the urinal therebetween. The mutual deformation of the inner surface of the thighs and of the wall of the urinal where the thighs are in contact with the urinal, keeps the urinal securely in place without any other support while it is being filled. There is no need to use the handle except to facilitate putting it in place and, indeed, a handle is not strictly necessary, although it is a considerable convenience in placing it, and in moving it when filled.

The embodiment of FIG. 2 has means 20 formed integrally with the front wall 21 of the urinal for facilitating manual placement and removal, these means containing a slot 22 into which a hand grip partially shown at 23 in FIG. 3 can be inserted from below. The slot 22 is closed at the top, a provision which is sufficient to keep the handle connected to the rest of the urinal while it is being held upright by hand. Preferably there is a friction fit of the handle 23 in the T-shaped slot 22, so that the handle will not fall out of the slot by its own weight.

In the embodiment of FIGS. 2 and 3 the rounded corners of the bottom 25 are located at the corners of a square and although the front and rear edges of the bottom are straight, the lateral edges are concave, as shown at 26 and 27. In the unstressed condition of the device, as shown in the single-dotted broken line 28, the rim of the container formed by the tops of the sidewalls is in the shape of a square with rounded corners. Its lateral sides could, in this case, be concave like the bottom, but it is preferred to have the rim straight at the side as well as the front and rear in order to provide more resistance to flexing. The bottom does not yield under lateral stress and a slight concavity reduces the pressure against the flesh, except at the front and rear ends where the pressure is most effective in providing stability of position. A further reduction of the pressure against the flesh without significant sacrifice of stability could be provided by making the rear wall less wide than the front wall as in FIG. 1, but no very great reduction of the pressure against the thighs is desirable at the rear top corners of the urinal, since it is important to cause the labia to disengage and open a clear passage.

The outline 28 of the unstressed outer edge of the rim of the urinal indicates that there is a slight taper to the container as a whole in its unstressed state, which facilitates manufacture by injection molding or by some other casting process, and also permits partial nesting for storage.

The deformed shape of the rim when the device is used, shown by the solid lines 30 in FIG. 2, still provides an indentation of the flesh of the user's thighs at the apex 31 produced by the deformed corner of the container wall, where a lateral wall meets the rear end wall. This apex helps to keep the container upright while in use, being aided also by the corresponding corner of the bottom and the general friction engagement of the lateral walls with the user's skin.

FIG. 3 shows the provision of "feet" constituted by the external downward protuberances 34 on the bottom 25 of the urinal. These provide more stability when the device is on a slightly uneven surface.

Figure 4:
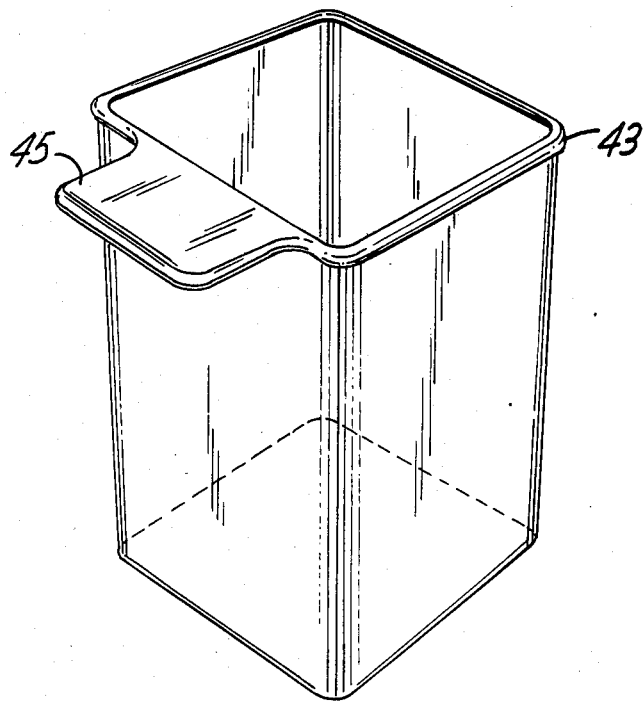

FIG. 4 is a perspective view of a third embodiment of urinal according to the invention, which can make use of a stiff plastic material rather than the kind of resiliently flexible material utilized in the first and second embodiments already described. The shape shown in FIG. 4, lends itself to inexpensive production and storage with the objective of making possible a device of such low cost that people will not hesitate to dispose of it after one use and of a shape suitable for dispensing in the washroom of a restaurant or other public place. An externally beaded rim is shown at 43 and a simple grip shown at 45 so that the thickness of the material can be essentially the same there as in the rim.

The capacity of the urinal is preferably about 1 liter for use by adults and about half a liter for use by small children. For the embodiment of FIG. 1, that makes the length and width conveniently substantially less than 10 centimeters and the height somewhat more than 10 centimeters, for example, 12 or 13 cm.

The embodiment of FIG. 4 is preferably of about the same size. Its width should not be reduced merely because of its rigidity by more than about 10%, because a width which will assure the spreading apart of the labia, especially the minor labia which are floppy and cover the urethra is much more important than the shape of the walls of the urinal and the contour shape of the rim.

The materials for the flexible-wall embodiments, such as shown in FIGS. 1–3, are preferably materials like polyethelene, which are flexible, cheap and not difficult to clean, whereas for the stiff type shown in FIG. 4 which do not need to yield very much, a much wider range of materials well known in the art of making molded plastic articles is available.

The several types of handles illustrated in the drawings do not, of course, exhaust the possibilities for manual holding means to assist placement and removal.

Although the urinals of this invention do not attempt to catch possible random squirting of urine from between the labia by closely surrounding and fitting the labia, they succeed in still a better way in dealing with such squirting, as well as dribble and trickle, by preventing both the minor and the major labia from interfering with urination.

It will thus be seen that although the invention has been described with reference to several illustrative examples, further modifications and variations are possible within the inventive concept and, in particular, features shown in connection with one embodiment may in many cases be usefully incorporated in other embodiments.

What is claimed is:

1. A urinal of light, relatively stiff material capable of facilitating hygienic and convenient urination by a female person in an erect position, comprising a substantially flat bottom of substantially rectangular shape and having a front to back length not more than 50% greater than its width and corners sufficiently round to eliminate sharp edges, and having also side walls integral with said bottom upstanding therefrom to a height exceeding the front to back length of the bottom, so as to provide a capacity of between one-half liter and one liter, said sidewalls being composed of lateral walls and front and rear end walls joined together with said bottom to form a container having a rim of approximately rectangular contour and a width of at least 8 cm, the stiffness of said container at said rim and the width of said rim being sufficiently great to deform a female user's thighs to an extent which spreads her labia apart out of the way of a stream of urine discharged by her urethra to minimize interference of the labia with urination, and reinforcement means for giving the rim more stiffness than the wall portion below the rim.

2. Urinal according to claim 1 in which said bottom is substantially rectangular and in which said opening at the top in the unstressed condition of said sidewalls is substantially a rectangle of dimensions just sufficiently larger than the dimensions of said bottom to enable partial nesting for storage of one urinal within another of the same shape.

3. A urinal according to claim 2, in which said bottom and said opening are both square.

4. Urinal according to claim 1 in which said means for facilitating placement are located on said hand holding front endwall and include connecting means on said front end sidewall for attachment of a detachable handle.

5. Urinal according to claim 1, in which said hand holding means for facilitating placement are located on said front end wall and include a protuberance of said front end sidewall of a shape suitable for grasping by hand.

6. Urinal according to claim 1 having also means near the front of the rim for facilitating holding of the urinal by one hand of the user for placement and displacement thereof.

7. A urinal according to claim 1, in which means for facilitating manual placement and displacement thereof by one hand of a user are provided on said front end wall at the top edge thereof.

8. A urinal according to claim 1, in which the shape of said sidewalls in such that the perimeter of the top of said urinal is not less than that of its bottom does not exceed the perimeter of its bottom by more than 10%.

9. A urinal according to claim 1 formed in one piece of molded plastic.

10. A urinal according to claim 1, in which external foot proturberances are provided in the respective regions of said corners of said bottom.

11. A method of clean erect urination for a female person comprising the steps of:

obtaining a container in the form of an open-top flat-bottomed box of a capacity between one-half liter and one and one-half liters having a front, back and lateral sides, extending from the bottom upwards to a rim which is substantially parallel to the bottom, said container being of sufficient width, at least in the region of the rim, to exert lateral pressure which is sufficient to deform the flesh of the thighs adjacent to the rim of the container when inserted in the user's crotch and squeezed and to deform the user's thighs to an extent which spreads the labia of her vulva apart out of the way of urine discharged by her urethra;

inserting said container in the female person's crotch and squeezing it, especially at the top of the container, between the thighs sufficiently to deform the thigh in such a way as to spread apart the labia and give a clear path from the urethra into the container for urine discharged from the urethra;

urinating into the container while maintaining lateral pressure against the container from the thighs, and thereafter removing the container by hand.

* * * * *